(12) United States Patent
Weaver et al.

(10) Patent No.: US 8,506,684 B2
(45) Date of Patent: Aug. 13, 2013

(54) GAS RELEASE DEVICES FOR EXTRACORPOREAL FLUID CIRCUITS AND RELATED METHODS

(75) Inventors: Colin Weaver, Pleasanton, CA (US);
Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 334 days.

(21) Appl. No.: 12/968,686

(22) Filed: Dec. 15, 2010

(65) Prior Publication Data
US 2012/0152118 A1 Jun. 21, 2012

(51) Int. Cl.
*B01D 19/00* (2006.01)
(52) U.S. Cl.
USPC .............. 95/259; 95/260; 96/206; 96/219; 604/5.04
(58) Field of Classification Search
USPC ............ 95/259, 260; 96/206, 219; 604/5.04
See application file for complete search history.

(56) References Cited

U.S. PATENT DOCUMENTS

| | | | |
|---|---|---|---|
| 3,946,731 A | 3/1976 | Lichtenstein | |
| 3,982,538 A | 9/1976 | Sharpe | |
| 3,985,135 A | 10/1976 | Carpenter et al. | |
| 3,996,027 A * | 12/1976 | Schnell et al. | 95/261 |
| 4,014,206 A | 3/1977 | Taylor | |
| 4,026,669 A | 5/1977 | Leonard et al. | |
| 4,061,031 A * | 12/1977 | Grimsrud | 73/200 |
| 4,137,160 A | 1/1979 | Ebling et al. | |
| 4,187,057 A | 2/1980 | Xanthopoulos | |
| 4,231,370 A | 11/1980 | Mroz et al. | |
| 4,370,983 A | 2/1983 | Lichtenstein | |
| 4,459,139 A | 7/1984 | vonReis et al. | |
| 4,488,961 A | 12/1984 | Spencer | |
| 4,530,759 A | 7/1985 | Schal | |
| 4,572,724 A | 2/1986 | Rosenberg et al. | |
| 4,590,227 A | 5/1986 | Nakamura et al. | |
| 4,643,713 A | 2/1987 | Viitala | |

(Continued)

FOREIGN PATENT DOCUMENTS

| | | |
|---|---|---|
| DE | 102005001779 | 9/2006 |
| EP | 0327136 | 8/1989 |

(Continued)

OTHER PUBLICATIONS

Gambro®, "DEHP-Free Cartridge Blood Sets", © Nov. 2004, Gambro, Inc, Lakewood, CO, 4 pp.

(Continued)

*Primary Examiner* — Duane Smith
*Assistant Examiner* — Douglas Theisen
(74) *Attorney, Agent, or Firm* — Fish & Richardson P.C.

(57) ABSTRACT

In one aspect, a gas release device for removing gas from a bodily liquid in extracorporeal circuitry is described. The device includes an elongate vertical portion and a flared portion that extends outwardly from the elongate vertical portion. The device also includes an inlet port for delivering a bodily liquid into the device, and an outlet port for evacuating the bodily liquid from the device. The inlet port is positioned below the elongate vertical portion and the outlet port is positioned below the flared portion such that bodily liquid traveling from the inlet toward the outlet is forced around the flared portion to cause air bubbles in the bodily liquid to be re-circulated back toward the inlet port.

26 Claims, 18 Drawing Sheets

(56) References Cited

U.S. PATENT DOCUMENTS

| | | | |
|---|---|---|---|
| 4,662,906 A | 5/1987 | Matkovich et al. |
| 4,695,385 A | 9/1987 | Boag |
| 4,702,675 A | 10/1987 | Aldrovandi et al. |
| 4,702,829 A | 10/1987 | Polaschegg et al. |
| 4,888,004 A | 12/1989 | Williamson et al. |
| 4,997,464 A | 3/1991 | Kopf |
| 5,061,236 A | 10/1991 | Sutherland et al. |
| 5,330,425 A | 7/1994 | Utterberg |
| 5,425,173 A | 6/1995 | Moss et al. |
| 5,441,636 A | 8/1995 | Chevallet et al. |
| 5,460,490 A | 10/1995 | Carr et al. |
| 5,498,338 A | 3/1996 | Kruger et al. |
| 5,540,265 A | 7/1996 | Polaschegg et al. |
| 5,578,070 A | 11/1996 | Utterberg |
| 5,591,344 A | 1/1997 | Kenley et al. |
| 5,614,677 A | 3/1997 | Wamsiedler et al. |
| 5,628,908 A | 5/1997 | Kamen et al. |
| 5,643,205 A | 7/1997 | Utterberg |
| 5,651,893 A | 7/1997 | Kenley et al. |
| 5,674,390 A | 10/1997 | Matthews et al. |
| 5,674,404 A | 10/1997 | Kenley et al. |
| 5,690,831 A | 11/1997 | Kenley et al. |
| 5,711,883 A | 1/1998 | Folden et al. |
| 5,714,060 A | 2/1998 | Kenley et al. |
| 5,725,776 A | 3/1998 | Kenley et al. |
| 5,788,671 A | 8/1998 | Johnson |
| 5,849,065 A | 12/1998 | Wojke |
| 5,863,421 A | 1/1999 | Peter et al. |
| 5,928,177 A | 7/1999 | Brugger et al. |
| 5,938,634 A | 8/1999 | Packard |
| 5,989,423 A | 11/1999 | Kamen et al. |
| 6,179,801 B1 | 1/2001 | Holmes et al. |
| 6,196,987 B1 | 3/2001 | Holmes et al. |
| 6,200,287 B1 | 3/2001 | Keller et al. |
| 6,231,537 B1 | 5/2001 | Holmes et al. |
| 6,234,989 B1 | 5/2001 | Brierton et al. |
| 6,280,406 B1 | 8/2001 | Dolecek et al. |
| 6,336,916 B1 | 1/2002 | Bormann et al. |
| 6,337,049 B1 | 1/2002 | Tamari |
| 6,361,518 B1 | 3/2002 | Brierton et al. |
| 6,383,158 B1 | 5/2002 | Utterberg et al. |
| 6,409,696 B1 | 6/2002 | Toavs et al. |
| 6,497,674 B1 | 12/2002 | Steele et al. |
| 6,497,676 B1 | 12/2002 | Childers et al. |
| 6,514,225 B1 | 2/2003 | Utterberg et al. |
| 6,536,278 B1 | 3/2003 | Scagliarini |
| 6,695,803 B1 | 2/2004 | Robinson et al. |
| 6,725,726 B1 | 4/2004 | Adolfs et al. |
| 6,730,055 B2 | 5/2004 | Bainbridge et al. |
| 6,743,201 B1 | 6/2004 | Dönig et al. |
| 6,755,801 B2 | 6/2004 | Utterberg et al. |
| 6,764,460 B2 | 7/2004 | Dolecek et al. |
| 6,790,195 B2 | 9/2004 | Steele et al. |
| 6,852,090 B2 | 2/2005 | Burbank et al. |
| 6,887,214 B1 | 5/2005 | Levin et al. |
| 6,979,309 B2 | 12/2005 | Burbank et al. |
| 7,021,148 B2 | 4/2006 | Kuhn et al. |
| 7,115,107 B2 | 10/2006 | Delnevo et al. |
| 7,238,164 B2 | 7/2007 | Childers et al. |
| 7,476,209 B2 | 1/2009 | Gara et al. |
| 7,517,387 B2 | 4/2009 | Chevallet et al. |
| 7,603,907 B2 | 10/2009 | Reiter et al. |
| 7,621,983 B2 | 11/2009 | Neri |
| 7,871,391 B2 * | 1/2011 | Folden et al. ............... 604/6.09 |
| 7,892,331 B2 | 2/2011 | Childers et al. |
| 7,892,332 B2 | 2/2011 | Prisco et al. |
| 7,905,853 B2 | 3/2011 | Chapman et al. |
| 8,110,104 B2 | 2/2012 | Crnkovich et al. |
| 2002/0014462 A1 | 2/2002 | Muller |
| 2002/0072718 A1 | 6/2002 | Brugger et al. |
| 2002/0179527 A1 | 12/2002 | Yao |
| 2004/0019312 A1 | 1/2004 | Childers et al. |
| 2004/0238416 A1 | 12/2004 | Burbank et al. |
| 2005/0054968 A1 | 3/2005 | Giannella |
| 2005/0126998 A1 | 6/2005 | Childers |
| 2005/0131332 A1 | 6/2005 | Kelly et al. |
| 2005/0132826 A1 | 6/2005 | Teugels |
| 2005/0230292 A1 | 10/2005 | Beden et al. |
| 2007/0078369 A1 | 4/2007 | Tamari |
| 2007/0086924 A1 | 4/2007 | Moses |
| 2007/0106198 A1 | 5/2007 | Folden et al. |
| 2007/0112297 A1 | 5/2007 | Plahey et al. |
| 2007/0193940 A1 | 8/2007 | Duchamp et al. |
| 2007/0269340 A1 | 11/2007 | Dannenmaier et al. |
| 2008/0275364 A1 | 11/2008 | Conway et al. |
| 2009/0012449 A1 | 1/2009 | Lee et al. |
| 2009/0071911 A1 | 3/2009 | Folden et al. |
| 2009/0084718 A1 | 4/2009 | Prisco et al. |
| 2009/0084719 A1 | 4/2009 | Childers et al. |
| 2009/0084721 A1 | 4/2009 | Yardimci et al. |
| 2009/0101576 A1 | 4/2009 | Rohde et al. |
| 2009/0216211 A1 | 8/2009 | Beden et al. |
| 2009/0320684 A1 | 12/2009 | Weaver et al. |
| 2010/0133189 A1 | 6/2010 | Maierhofer et al. |
| 2010/0206784 A1 | 8/2010 | Weaver et al. |
| 2010/0222735 A1 | 9/2010 | Plahey et al. |
| 2010/0292627 A1 | 11/2010 | Caleffi et al. |
| 2011/0120946 A1 | 5/2011 | Levin et al. |

FOREIGN PATENT DOCUMENTS

| | | |
|---|---|---|
| EP | 0458041 | 11/1991 |
| EP | 0728509 | 8/1996 |
| EP | 0887100 | 12/1998 |
| EP | 1529545 | 5/2005 |
| EP | 1547630 | 6/2005 |
| EP | 1728526 | 12/2006 |
| EP | 1894587 | 3/2008 |
| EP | 2 226 087 | 9/2010 |
| JP | 2003180834 | 7/2003 |
| JP | 2005530543 | 10/2005 |
| WO | WO 9702056 | 1/1997 |
| WO | WO9640322 A3 | 3/1997 |
| WO | WO 0108722 | 2/2001 |
| WO | WO0150949 A1 | 7/2001 |
| WO | WO 0164312 | 9/2001 |
| WO | WO0226286 A2 | 4/2002 |
| WO | WO2004000391 A1 | 12/2003 |
| WO | WO 2005/044341 | 5/2005 |
| WO | WO2005044340 A1 | 5/2005 |
| WO | WO2005065745 A1 | 7/2005 |
| WO | WO 2005077490 | 8/2005 |
| WO | WO2008002370 | 1/2008 |

OTHER PUBLICATIONS

Gambro®, "Prisma® HF 1000, For Increased Filtration Capacity", © Aug. 2001, Gambro Renal Products, Inc., Lakewood, CO, 2 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Gambro®, "Prismaflex™, Anticipating Critical Care needs and taking our innovative response . . . to new heights", © 2004, Gambro Inc., Lakewood, CO, 8 pp.

Manns, Markus et al., "The acu-men: A new device for continuous renal replacement therapy in acute renal failure," Kidney International, vol. 54, pp. 268-274, 1998.

Acu-men, Acute Dialysis machine Operating Instructions, Software Version 1.0, Fresenius MY acu-men, Jan. 5, 1996 (OP), 146 pages.

* cited by examiner

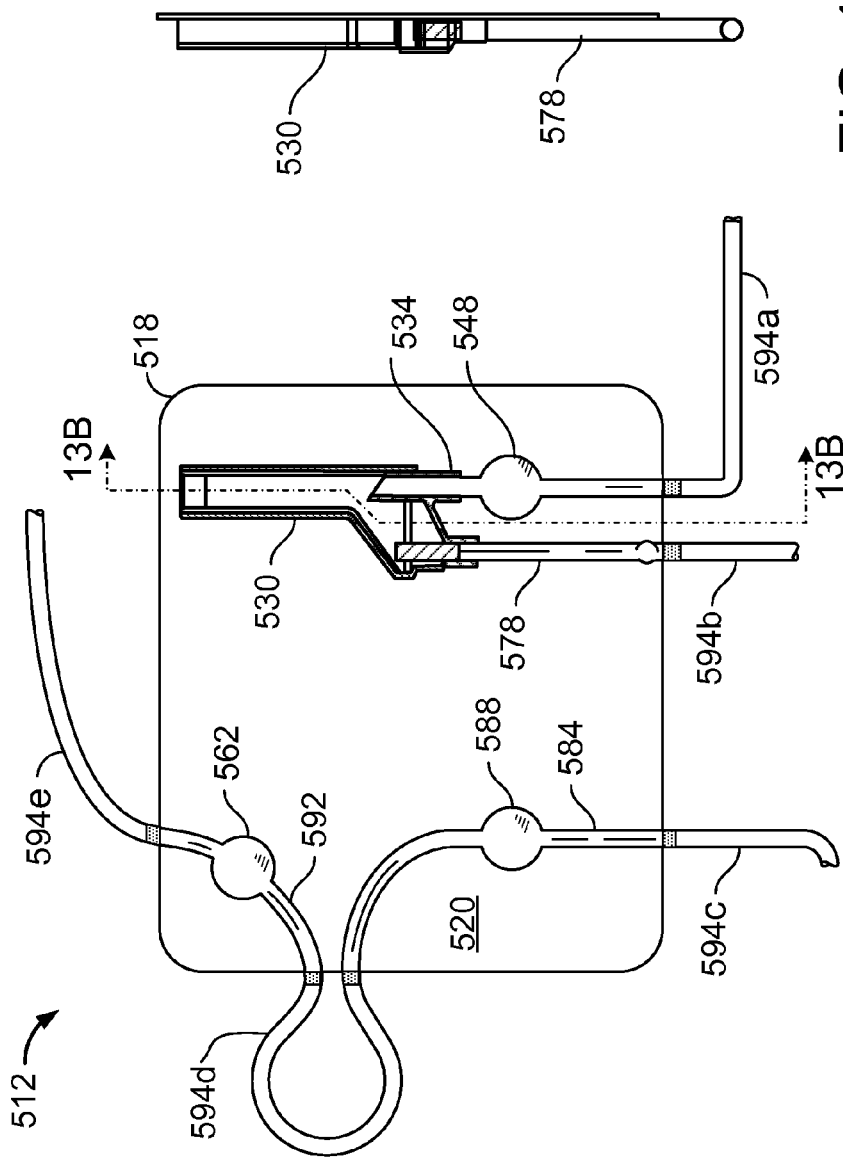

GAS RELEASE DEVICES FOR EXTRACORPOREAL FLUID CIRCUITS AND RELATED METHODS

TECHNICAL FIELD

This disclosure relates to gas release devices for extracorporeal fluid circuits and related methods.

BACKGROUND

Hemodialysis removes toxic substances and metabolic waste from the bloodstream using an extracorporeal circuit with components designed to perform ultrafiltration and diffusion on the blood. Before the blood is returned to the body, air bubbles are removed from the blood to reduce the risk of embolisms.

SUMMARY

In one aspect, a gas release device for removing gas from a bodily liquid in extracorporeal circuitry is described. The device includes an elongate vertical portion and a flared portion that extends outwardly from the elongate vertical portion. The device also includes an inlet port for delivering a bodily liquid into the device, and an outlet port for evacuating the bodily liquid from the device. The inlet port is positioned below the elongate vertical portion and the outlet port is positioned below the flared portion such that bodily liquid traveling from the inlet toward the outlet is forced around the flared portion to cause gas bubbles in the bodily liquid to be re-circulated back toward the inlet port.

In another aspect, a method of removing gas from blood in extracorporeal circuitry is described. The method includes passing blood through an inlet port and into an elongate vertical portion of a gas release device until upward motion of the bodily liquid is impeded by gravity, and passing the blood along a flared portion of the gas release device toward an outlet port such that gas bubbles in the blood are directed back toward the inlet port to be released through the elongate vertical chamber.

Implementations of the disclosed devices and methods may include one or more of the following features.

The gas release device can have a substantially flat geometry.

The gas release device can have a substantially tubular geometry.

In some implementations, the elongate vertical portion has a height of about 2.54 inches to about 3.10 inches, e.g., 2.82 inches.

The elongate vertical portion can have a hollow volume of about 0.70 cubic inches to about 1.33 cubic inches.

In certain implementations, a first side of the flared portion extends outwardly from the elongate vertical portion at an angle of about 44° to about 54°, e.g., 49°, relative to a centerline of the elongate vertical portion.

In some implementations, a first side of the flared portion extends outwardly from the elongate vertical portion at an angle of about 27° to about 33°, e.g., 30°, relative to a centerline of the elongate vertical portion.

The gas release device can include a main body, which defines the elongate vertical portion and the flared portion, and a two port cap, which defines the inlet and outlet ports.

In certain implementations, the inlet port is elevated above the outlet port with respect to the standard orientation of the gas release device. For example, the inlet port can be elevated at a height of about 0.29 inches to about 0.35 inches above the outlet port.

In some implementations, a bottom wall of the gas release device extends at an angle of about 54° to about 66°, e.g., 60°, relative to vertical, with respect to the standard orientation of the gas release device.

The gas release device can also include a dam between the inlet port and the outlet port.

The elongate vertical portion can have a height sufficient to maintain an interface between a first liquid in the vertical chamber and a second liquid in the gas release device when the first and second liquids are miscible and the second liquid is flowing through the gas release device.

In some cases, a clot filter is positioned in the gas release device. The clot filter can be positioned so that the liquid passes through the clot filter prior to passing through the outlet port.

In some implementations, the gas release device is incorporated as a component in a cassette-like integrated fluid circuit that is adapted to removably seat in a bodily liquid purification machine (e.g., a hemodialysis machine).

Methods can include passing a blood-compatible component, such as saline, through the inlet port, thereby filling the gas release device so that substantially no gas remains in the gas release device; and then passing the blood through the inlet port, thereby forming a liquid-liquid interface between the blood-compatible component and the blood.

Methods can also include forcing the blood over a dam. after passing the blood through the inlet port; and passing the blood out an outlet port after forcing the blood over the dam.

In some implementations, methods include passing the blood through a clot filter; and passing the blood through the outlet port after passing the blood through the clot filter. Passing blood through the inlet port can include passing blood through an inlet port of the gas release device that is elevated relative to the outlet port of the gas release device.

Implementations can include one or more of the following advantages.

In some implementations, the recirculation of unreleased gas bubbles within blood flowing through a gas release device can help to ensure the removal of gas from the blood flow.

In certain implementations, a gas release device promotes the removal of gas bubbles from a blood flow by redirecting unreleased gas bubbles back toward an inlet blood flow within the gas release device.

In some implementations gas release device has a geometry that promotes the removal of gas bubbles from a blood flow by taking advantage of the buoyancy of the gas bubbles.

Other aspects, features, and advantages are in the description, drawings, and claims.

DESCRIPTION OF DRAWINGS

FIG. 13A is a plan view of a cassette-like integrated extracorporeal circuit.

FIG. 13B is a cross-sectional view of the cassette-like integrated extracorporeal circuit of FIG. 13A, taken along line 13B-13B.

DETAILED DESCRIPTION

A fluid circuit, such as an extracorporeal fluid circuit used in filtering blood from a patient during hemodialysis, can be provided with a gas release device having a geometry designed to promote the removal of air bubbles from a blood flow, as the blood flow travels from an inlet of the gas release device toward an outlet of the gas release device, by redirecting unreleased air bubbles back toward the inlet.

System Overview

Figure 1:
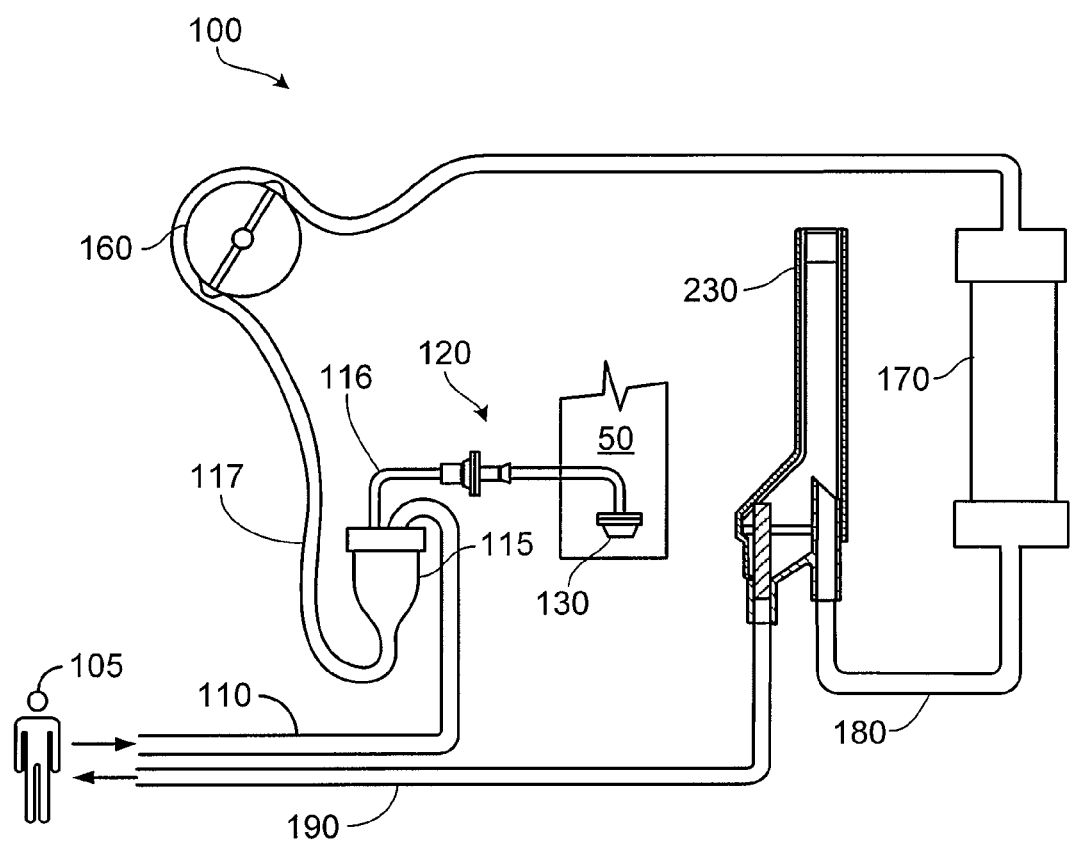
FIG. 1 is a schematic view of a hemodialysis system.

Referring to FIG. 1, an extracorporeal circuit 100 includes tubing through which the blood flows and components for filtering and performing dialysis on the blood. Blood flows from a patient 105 through arterial tubing 110. Blood drips into a drip chamber 115 where a connecting tube 116 from the drip chamber 115 attaches to an arterial pressure sensor assembly 120 on a hemodialysis machine 50 that determines the pressure of the blood on the arterial side of the circuit 100. The arterial pressure sensor assembly 120 includes a pressure transducer 130, which can be mounted within a dialysis machine 50, so that the pressure of blood flowing through the circuit 100 on the arterial side can be monitored.

A pump 160, such as a peristaltic pump, forces the blood to continue along the path through a line 117 of the circuit 100. The blood then flows to a dialyzer 170, which separates waste products from the blood.

After passing through the dialyzer 170, the blood flows through venous tubing 180 towards a gas release device 230 in which gas (e.g., air) in the blood can escape before the blood continues to the patient 105. During treatment, should air be present in the blood, the blood with air bubbles flows in through the bottom of the gas release device 230. The upper motion of the blood is impeded by gravity and becomes stagnant, while the air continues to the top of the gas release device 230 where it is vented out to the atmosphere. After leaving the gas release device 230, the blood travels through a venous line 190 and back to the patient 105.

Gas Release Device

Figure 2A:
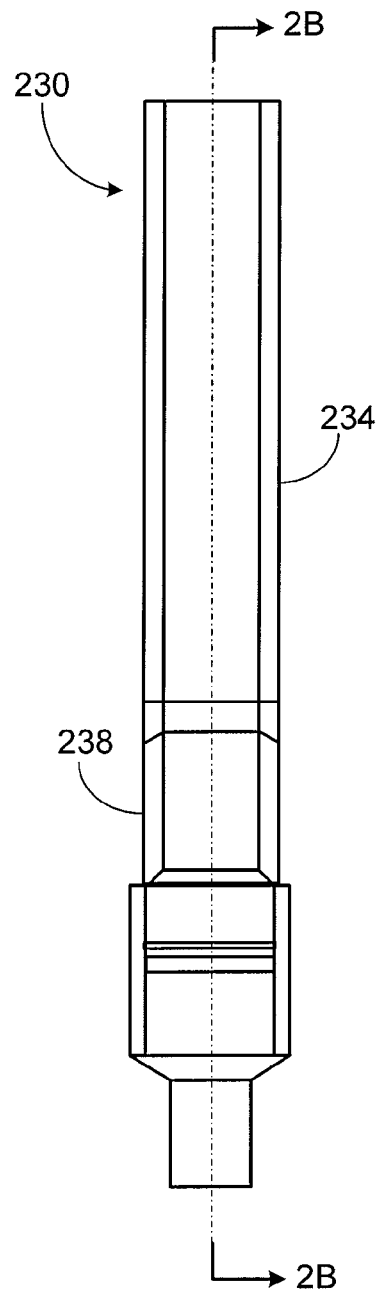
FIG. 2A is a back view of a gas release device of the system of FIG. 1.
Figure 2B:
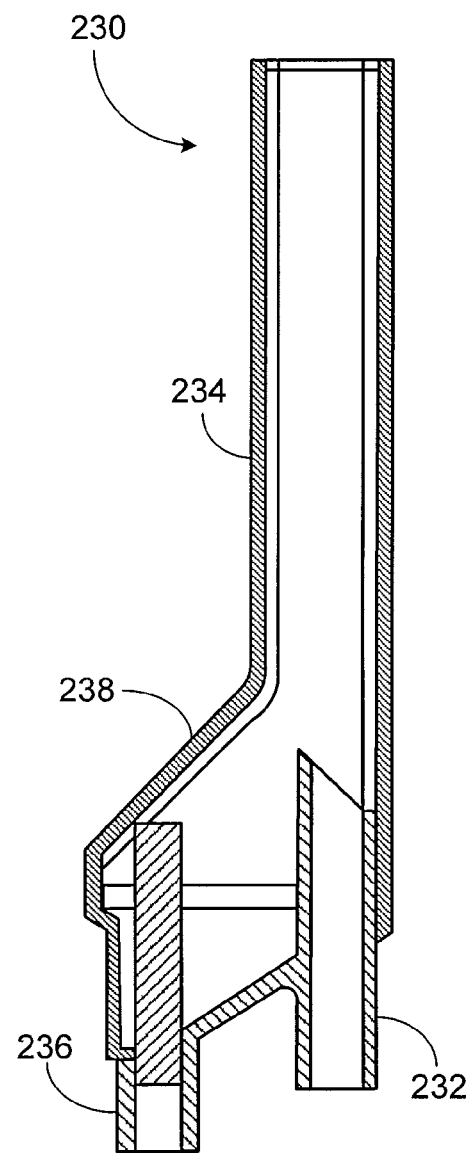
FIG. 2B is a cross-sectional side view of the gas release device of FIG. 2A, taken along line 2B-2B.
Figure 3:
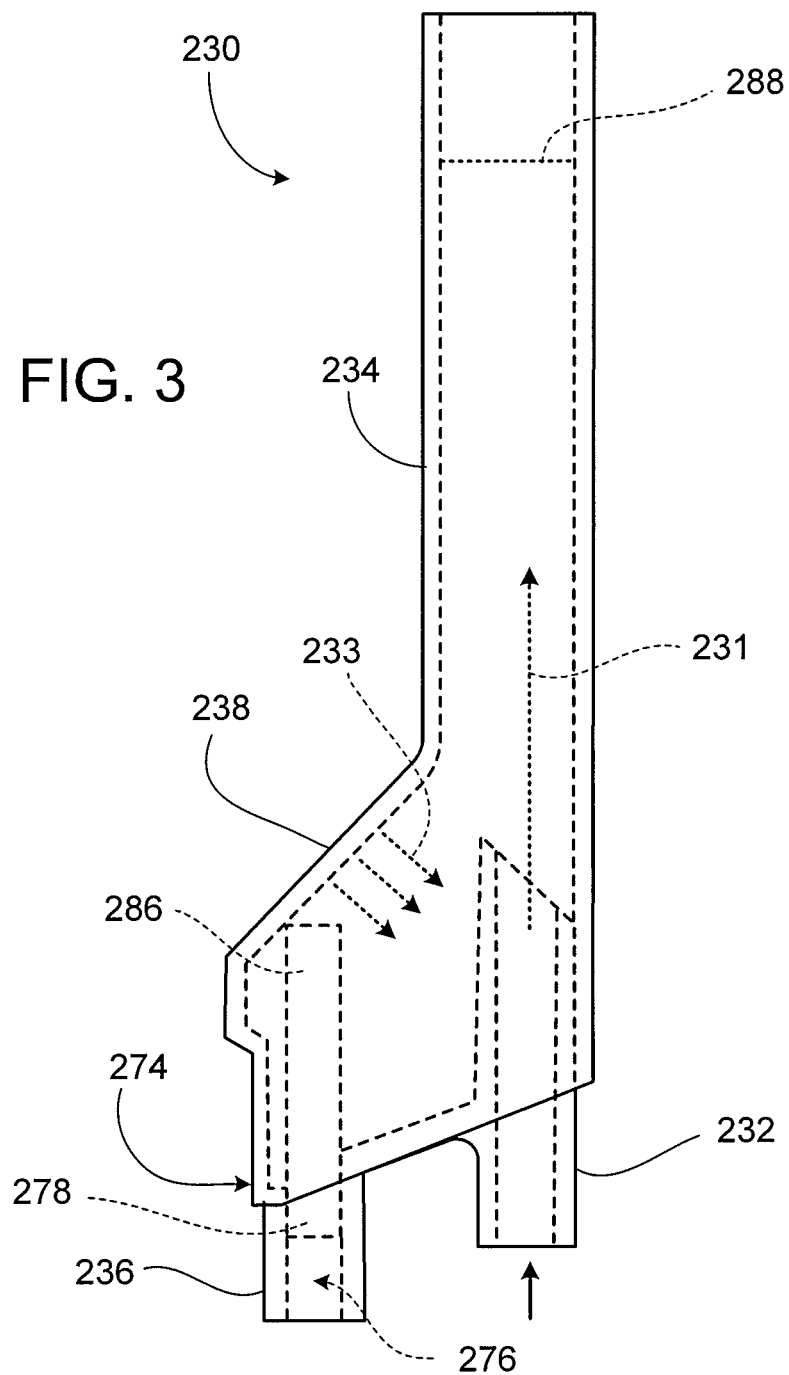
FIG. 3 is a side view of the gas release device of FIG. 2A.

Referring to FIGS. 2A & 2B, the gas release device 230 is substantially hollow for filling with a liquid and includes an inlet (inlet port 232) that is positioned below an elongate vertical portion 234 and an outlet (outlet port 236) positioned below a flared (e.g., beveled) portion 238. As illustrated in FIG. 3, as blood flows through the gas release device 230, at least some air bubbles in the blood flow may rise straight up (arrows 231) and are released through the elongate vertical portion soon after the blood flow enters the gas release device through the inlet port 232. The geometry of the gas release device 230 is such that, as blood travels from the inlet port 232 to the outlet port 236, remaining air bubbles (i.e., air bubbles that are not released through the vertical portion when the blood flow first passes through the inlet), due their buoyancy, get directed around the flared portion 238 and are forced back towards the inlet port 232 (arrows 233), thereby increasing the likelihood that the air bubbles will be removed from the blood flow.

The gas release device 230 is formed of a material suitable for medical devices, that is, medical grade material. Plastics, such as polyvinylchloride, polycarbonate, polyolefins, polypropylene, polyethylene, or other suitable medical grade plastic can be used because of ease of their ease of manufacturing, ready availability and disposable nature. The gas release device 230 can be formed by molding, e.g., blow molding or injection molding. The gas release device 230 can be formed of a transparent or clear material so that the liquid flowing through the gas release device can be observed.

Figure 4:
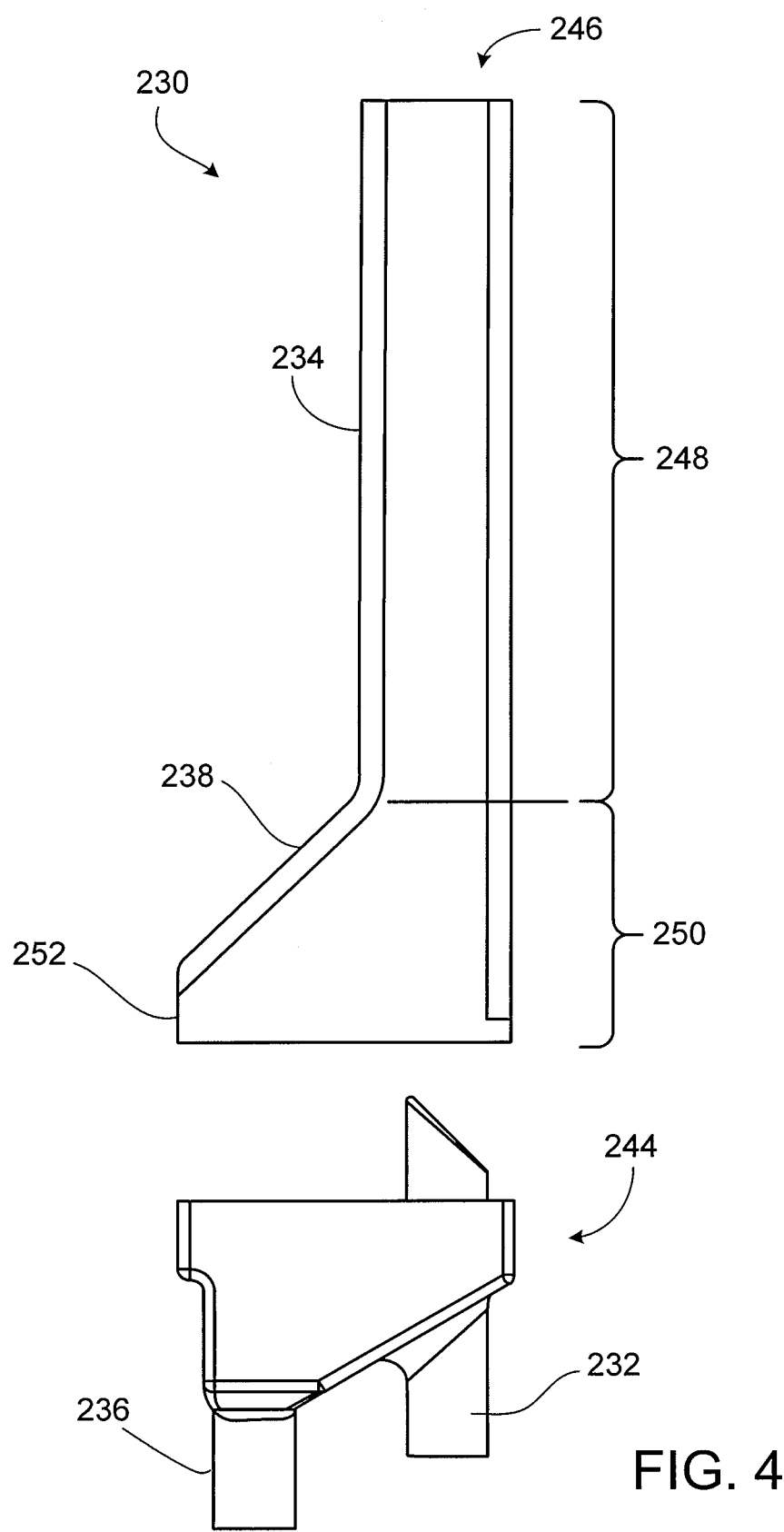
FIG. 4 is a side view of a main body and two-port cap that can be assembled to form the gas release device of FIG. 2A.
Figure 5A:
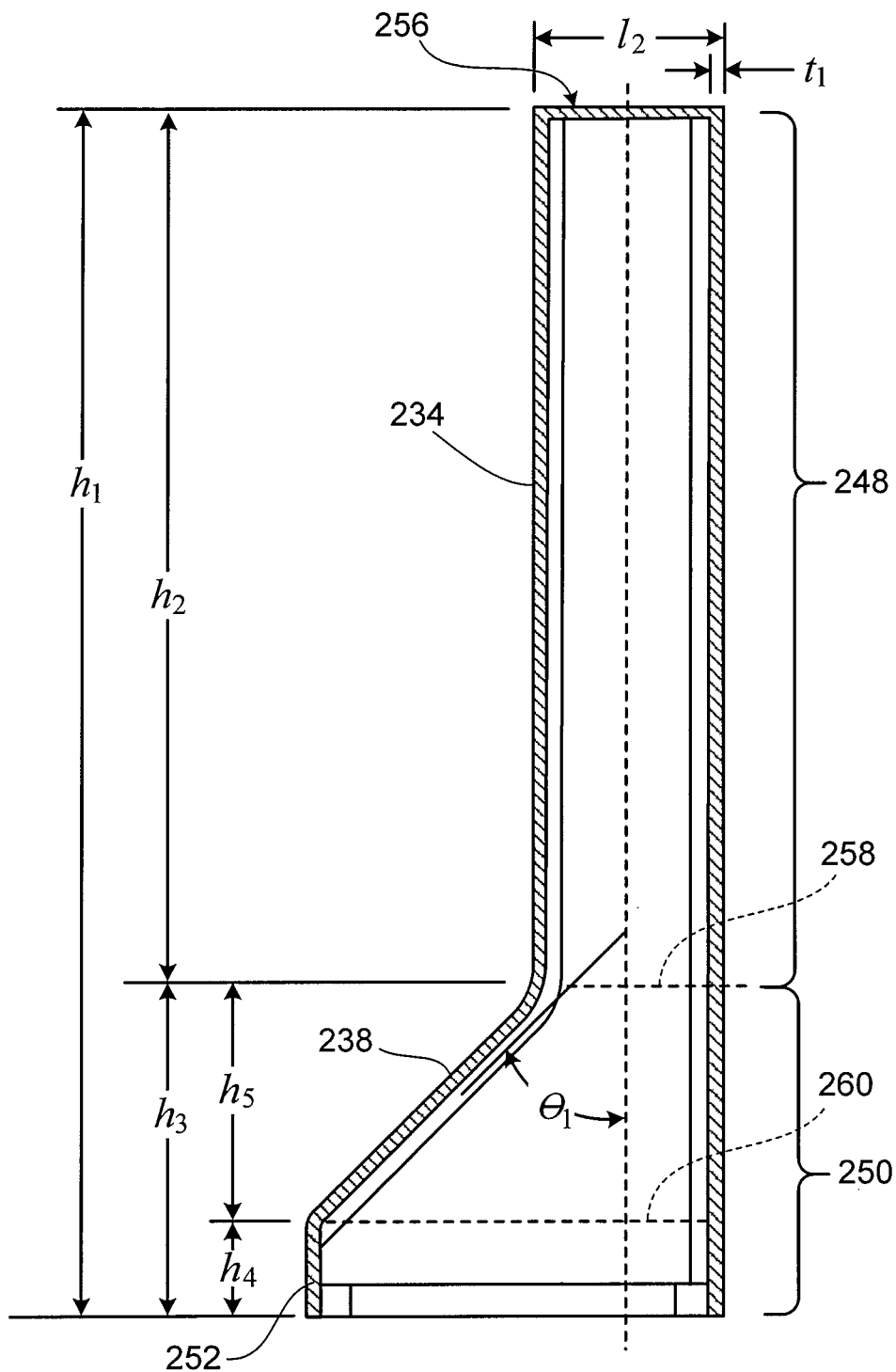
FIG. 5A is a cross-sectional side view of the main body of FIG. 4.
Figure 5B:
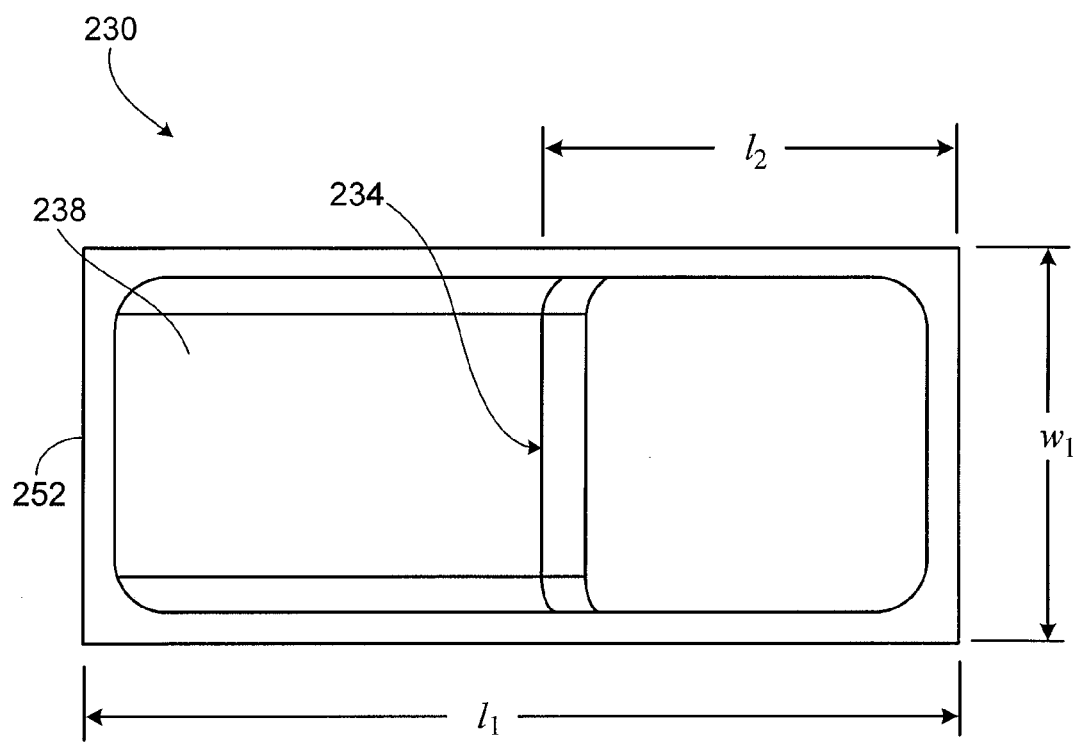
FIG. 5B is a top view of the main body of FIG. 4.

Referring to FIG. 4, the gas release device 230 is formed from two parts. A two port cap 244 forms a bottom part of the gas release device 230. A main body 246 forms a top part of the gas release device 230. The main body 246 has a top region 248 that defines the elongate vertical portion 234 and a bottom region 250 that defines the flared portion 238 as well as a base portion 252 that interfaces with the two port cap 244. Referring to FIGS. 5A & 5B, the main body 246 has a relatively flat design with an overall height h1 of about 3.56 inches to about 4.36 inches, e.g., 3.96 inches, a width w1 of about 0.57 inches to about 0.69 inches, e.g., 0.63 inches, and a length l1 of about 1.17 inches to about 1.43 inches, e.g., 1.38 inches. The walls of the main body 246 have a thickness t1 of about 0.036 to about 0.044, e.g., 0.040 inches.

In the top region 248 of the main body 246, the elongate vertical portion 234 has a height h2 of about 2.54 inches to about 3.10 inches, e.g., 2.82 inches, a length l2 of about 0.57 inches to about 0.69 inches, e.g., 0.63 inches, and width w1. The elongate vertical portion 234 extends from a first end 256 of the main body 246 to an upper end 258 of the bottom region 250.

The bottom region 250, including the base portion 252 and the flared portion 238, has an overall height h3 of about 1.03 inches to about 1.25 inches, e.g., 1.14 inches, with the base portion 252 having a height h4 of about 0.25 inches to about 0.31 inches, e.g., 0.28 inches, and the flared portion 238 having a height h5 of about 0.77 inches to about 0.95 inches, e.g., 0.86 inches. The base portion 252 and the flared portion 238 both have the same width w1.

The flared portion 238 extends from the upper end 258 of the bottom region 250 to an upper end 260 of the base portion 252. A first side of the flared portion 238 extends outwardly from the elongate vertical portion 234 at an angle $\theta_1$ of about 44° to about 54°, e.g., 49°, relative to a centerline of the elongate vertical portion 234, such that the flared portion 238 has a length l2 at the upper end 258 of the bottom region 250 and has a length l1 at the junction with the base portion 252.

Figure 6A:
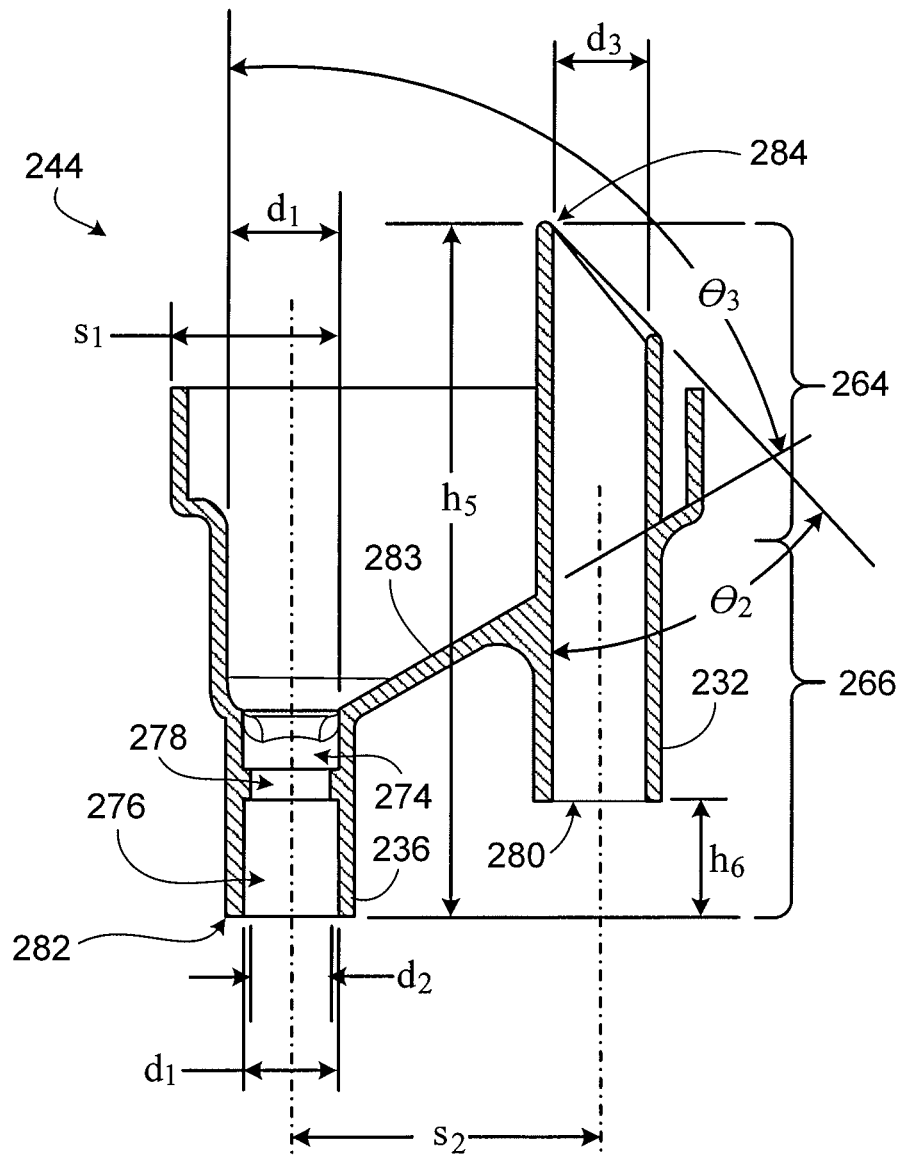
FIG. 6A is a cross-sectional side view of the two-port cap of FIG. 4.
Figure 6B:
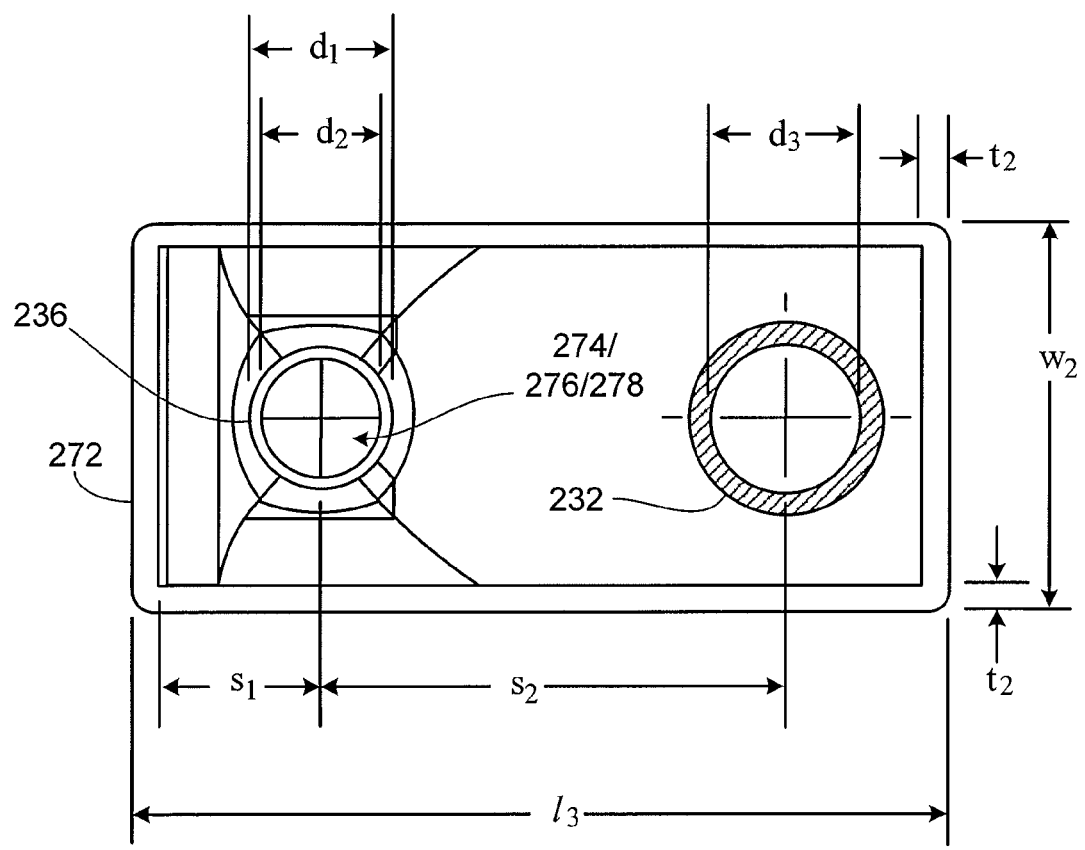
FIG. 6B is a top view of the two-port cap of FIG. 4.

Referring to FIGS. 6A & 6B, the two port cap 244 has an overall height h5 of about 1.68 inches to about 2.06 inches, e.g., 1.87 inches, an overall width w2 of about 0.63 inches to about 0.77 inches, e.g., 0.70 inches, and an overall length l3 of about 1.31 inches to about 1.61 inches, e.g., about 1.46 inches, and includes an upper region 264, which interfaces with the base portion 252 of the main body 246, and a lower region 266. The two port cap 244 also includes the inlet port 232 and the outlet port 236. The walls of the two port cap 244 have thickness t2 of about 0.036 to about 0.044, e.g., 0.040 inches.

The centerline of the outlet port 236 is arranged at a distance s1 of about 0.26 inches to about 0.32 inches, e.g., about 0.29 inches from an inner surface of a first sidewall 272 of the upper region 264. The outlet port includes a first counter bore hole 274 having a diameter d1 of about 0.23 inches to about 0.29 inches, e.g., about 0.26 inches, which extends from an interior of the two port cap 244, and a second counter bore hole 276 also having diameter d1, which extends from an exterior of the two port cap 244. A conduit 278, having diameter d2 of about 0.20 inches to about 0.24 inches, e.g., 0.22 inches, provides for fluid communication between the first and second counter bore holes 274, 276 and is centered around the same centerline as the first and second counter bore holes 274, 276.

The centerline of the inlet port 232 is arranged at a distance s2 of about 0.76 inches to about 0.92 inches, e.g., 0.84 inches, from the centerline of the outlet port 236. The inlet port 232 also has diameter d3 of about 0.23 inches to about 0.29 inches, e.g., about 0.26 inches. A first end 280 of the inlet port 232 is positioned at a height h6 of about 0.29 inches to about 0.35 inches, e.g., 0.32 inches, above a lower end 282 of the outlet port 236. A second end 284 of the inlet port 232 is formed at an angle $\theta_2$ of about 40° to about 50°, e.g., 45°, relative to the vertical y-axis. At its highest point, second end 284 of the inlet port 232 is positioned at height h5 above the lower end 282 of the outlet port 236. The two port cap 244 also includes a bottom wall 283 that extends at an angle $\theta_3$ of about 54° to about 66°, e.g., 60°. This difference in the height and relative positioning of the inlet and outlet ports 232, 236, as well as the geometry of the two port cap 244 help to contribute to the recirculation of un-released air bubbles.

When the two port cap 244 and the main body 246 are brought together they form the gas release device 230. As shown in FIG. 3, a clot filter 286 is positioned within the first counter bore hole 274 of the outlet port 236. Fluid flows through the clot filter 286 prior to flowing out of the outlet port 236.

Methods of Operation

Figure 7:
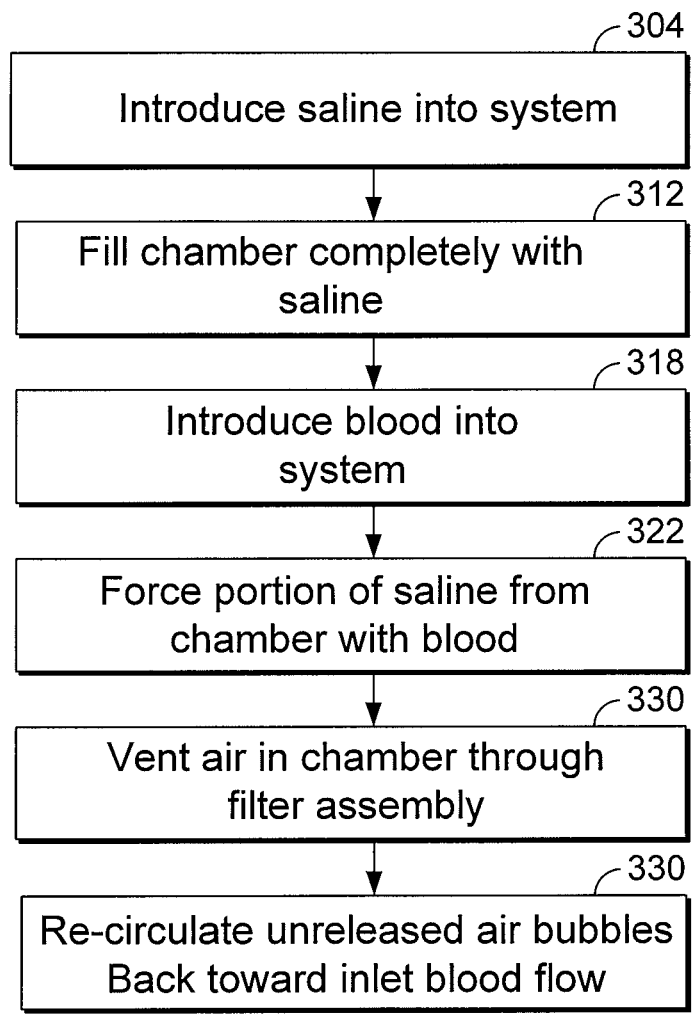
FIG. 7 is a flow diagram for using a gas release device in an extracorporeal circuit.

Referring to FIGS. 1 and 7, the gas release device 230 is in line in the extracorporeal fluid circuit of a system for fluid filtration and air removal. A first liquid that is compatible with the liquid to be filtered (the second liquid) is introduced into the system to prime the system (step 304). In hemodialysis, the first liquid is a blood compatible solution, such as saline. The saline flows through the arterial tubing 110 to the arterial pressure sensor assembly 120 so that the pressure of the liquid flowing through the circuit 100 on the arterial side can be monitored, as described above. The saline then flows through a portion of the channel that abuts the pump 160. The pump 160 forces the saline through the circuit 100. The saline then flows to the dialyzer 170. Next, the saline, or the first liquid, flows through the inlet 232 of the gas release device 230 and fills the gas release device (step 312). To fill the gas release device completely, venous line 190 can be clamped to create a positive pressure once the saline is introduced into the gas release device 230. Air is forced out the top of the gas release device 230 as saline fills the gas release device 230.

The second liquid, such as a bodily fluid, for example, blood, is then introduced into the system (step 318). The blood follows the same route as the saline and, for the most part, pushes the saline through the circuit 100. When the blood enters the gas release device 230, the blood forces the saline at the bottom of the gas release device 230 through the outlet port 232 (step 322). However, the blood does not displace all of the saline within the gas release device 230. Because of the height of the gas release device 230, the blood enters the gas release device 230 and only traverses part of the height of the gas release device 230 before flowing back down along a flow path to the outlet port (as shown in the gas release device formed of transparent material in FIG. 3). An interface 288 between the saline and the blood delineates the furthest extent of most of the blood within the gas release device 230. The interface 288 between the blood and saline can visually be observed and stretches across the entire width of the gas release device. Because blood and saline are not immiscible, there is some amount of mixing between the two fluids around the interface 288.

Unbound gas, or air, that is in the blood, such as air that is introduced by the dialyzer 170 or air that comes out of solution from the blood, rises as tiny air bubbles within the blood and saline until the air eventually vents out through the top of the gas release device 230 (step 330). Due at least in part to the geometry of the gas release device 230, at least some of the air bubbles rise straight up through the inlet port 232 and out of the top of the elongate vertical portion 234. The blood flows up into the elongate vertical portion 234 until geometry prevents further upward flow (step 312). Then, the blood is forced (e.g., pushed or pulled via operation of the pump 160) around the flared portion 238. As the blood is forced around the flared portion 238, remaining air bubbles (i.e., air bubbles that did not rise straight up through the inlet port 232 and out of the elongate vertical portion 234), due to their buoyancy and the geometry of the flared portion 238, are re-circulated back toward the inlet stream (blood entering through the inlet port 232) providing further opportunity for release of the remaining air bubbles through the elongate vertical portion 234.

It was previously believed that air bubbles could be removed from the blood by slowing the blood flow entering a gas release device by forcing the blood flow around a curve as it enters the device. It has now been discovered that it can also be beneficial to allow blood entering a gas removal device to rise straight up through an inlet and into a vertical chamber, thereby allowing gas (e.g., air bubbles in the blood) to rise straight up and be release though a top of the vertical chamber, and then force the blood flow along a flared portion before it exits the gas release device through an outlet, since this causes unreleased air bubbles to be re-circulated back toward the inlet blood flood and thereby increases the likelihood that the previously unreleased air bubbles will be released through the vertical chamber.

Throughout the circuit, the blood flows without a substantial air-blood interface. Although the blood does not come into contact with air and thus clotting is less likely to occur, the blood can pass through an optional filter 286 in the gas release device 230. In some implementations, after exiting the gas release device, the blood passes by or through one or more sensors, such as temperature or air detecting sensors.

Other Implementations

While certain implementations have been described above, other implementations are possible.

Figure 8:
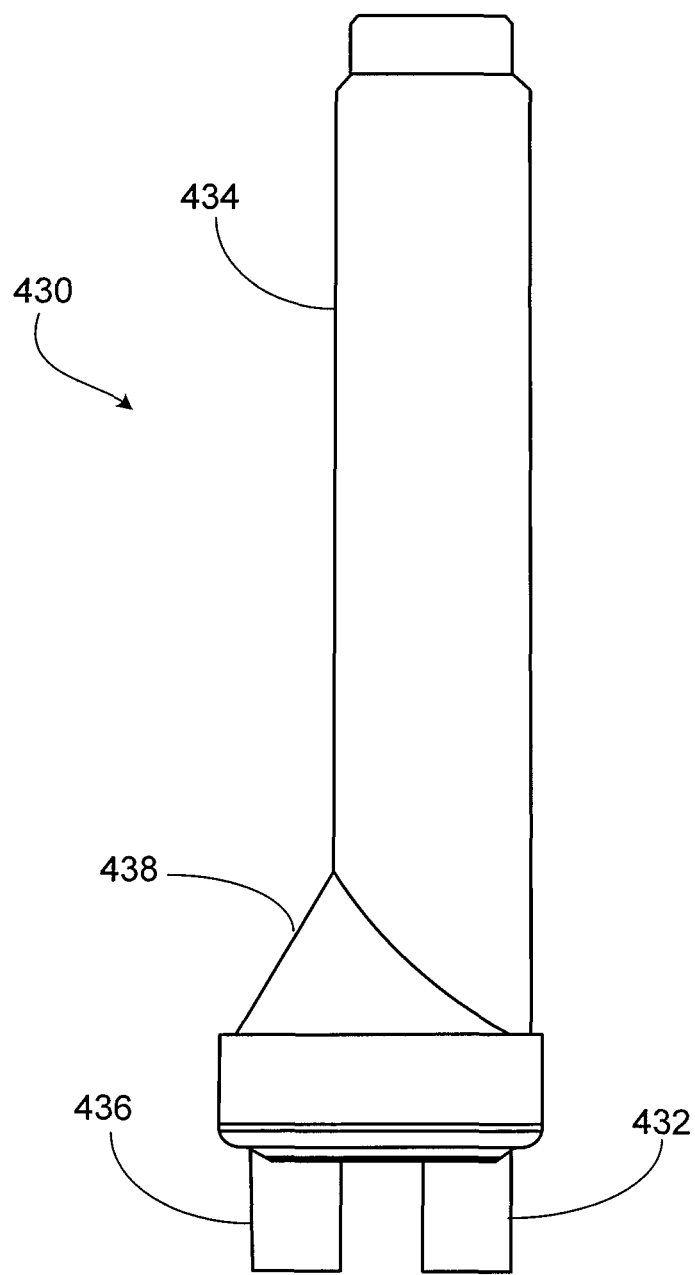
FIG. 8 is a side view of a gas release device having a substantially tubular geometry

As an example, although an implementation of a gas release device having a relatively flat design has been described, in some implementations, such as illustrated in FIG. 8, a gas release device 430 can have a tubular design. Like the flat gas release device described above with regard to FIGS. 2A-7B, the tubular gas release device also has a geometry that is designed to promote the removal of air bubbles from a blood flow, as the blood flow travels from an inlet of the gas release device toward an outlet of the gas release device, by redirecting unreleased air bubbles back toward the inlet.

Figure 9:
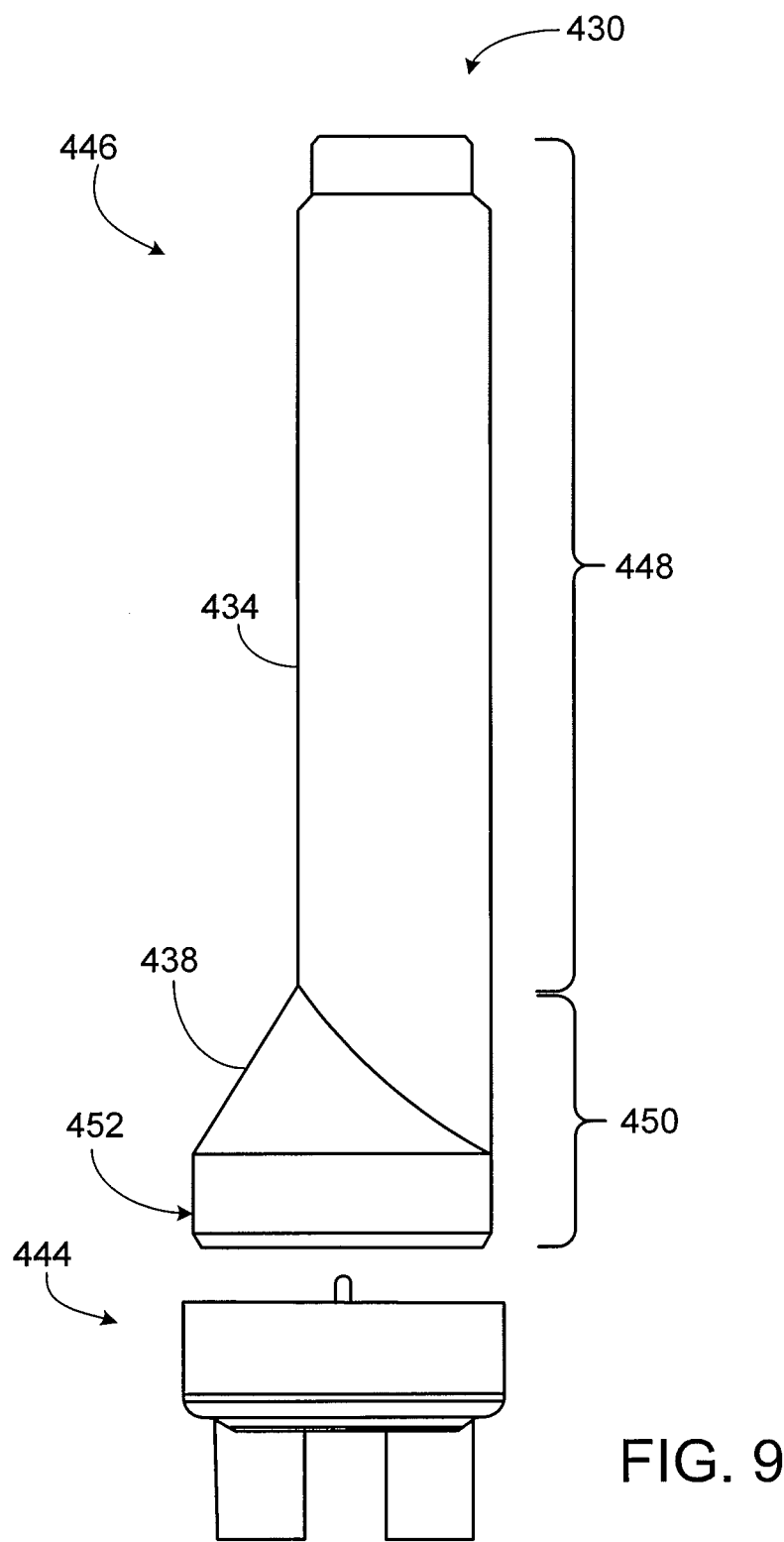
FIG. 9 is a side view of a main body and two-port cap that can be assembled to form the gas release device of FIG. 8.
Figure 10A:
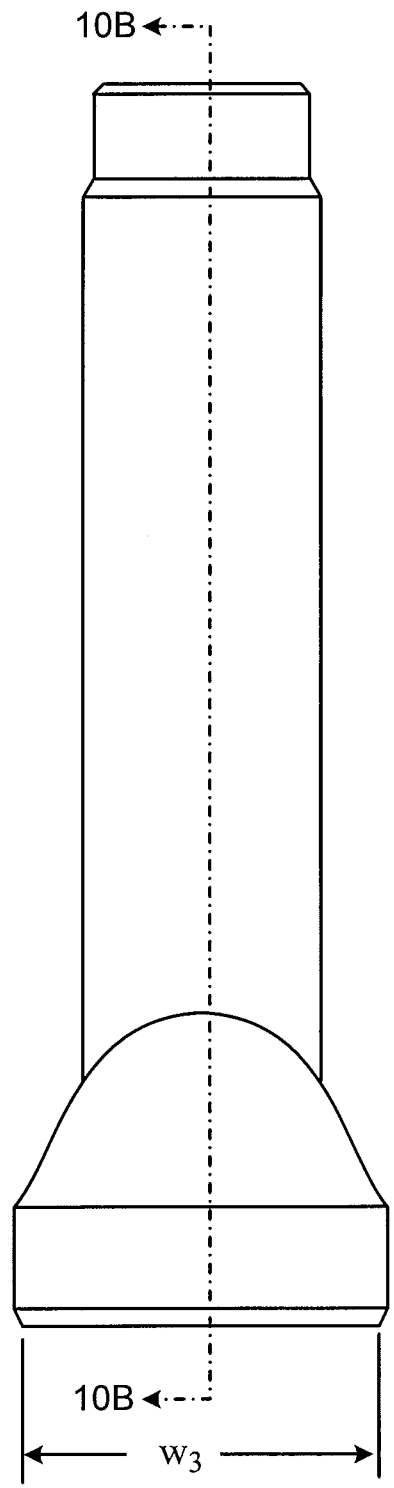
FIG. 10A is a front view of the main body of FIG. 9.
Figure 10B:
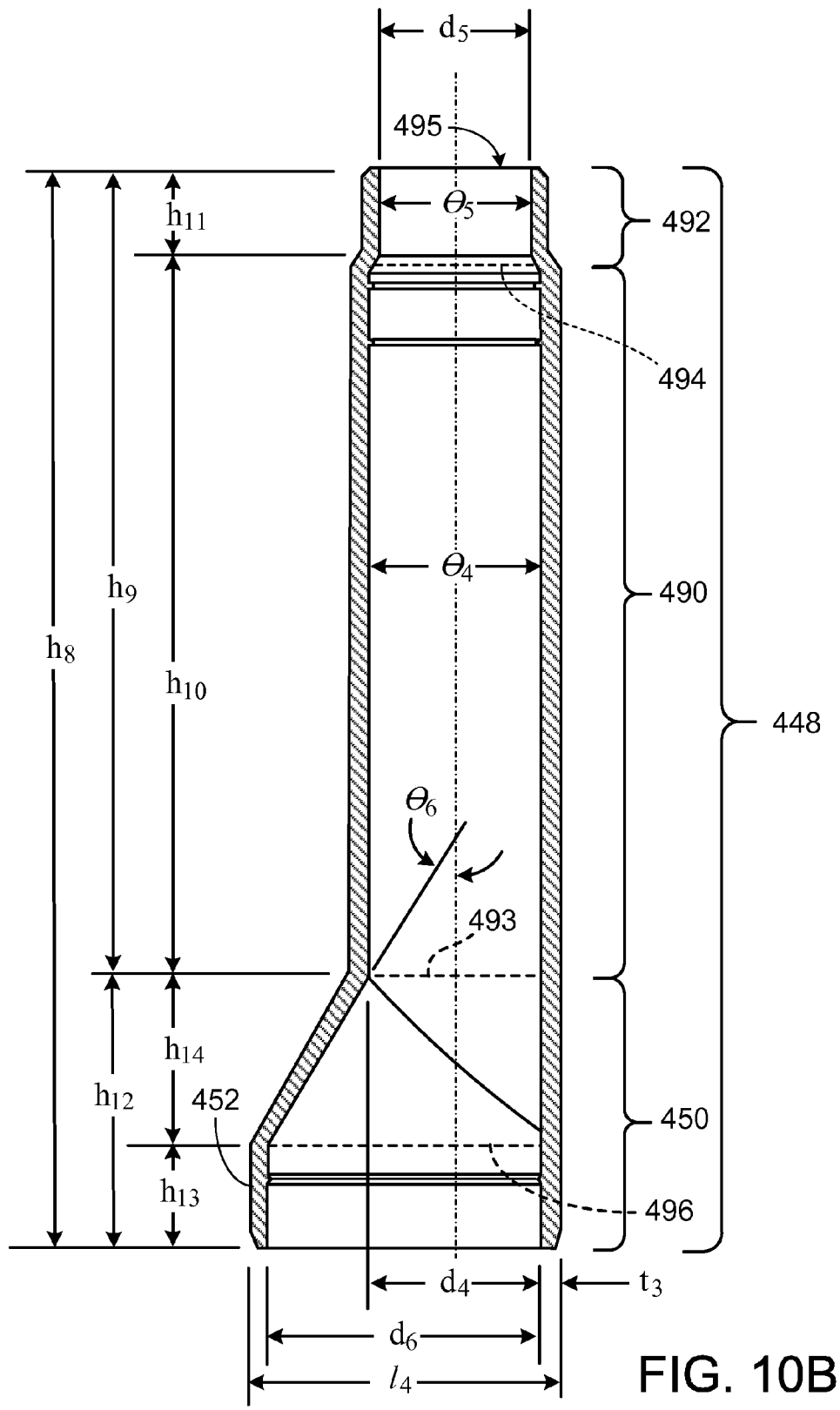
FIG. 10B is a cross-sectional side view of the main body of FIG. 10A, taken along line 10B-10B.

Referring to FIG. 9, the gas release device 430 is formed from two parts including a two port cap 444, which forms a bottom of the gas release device 430, and a main body 446, which forms a top of the gas release device 430. The main body 446 has a top region 448 that defines an elongate vertical portion 434 and a bottom region 450 that defines a flared portion 438 as well as a base portion 452 that interfaces with the two port cap 444. Referring to FIGS. 10A & 10B, the main body 446 has a relatively tubular design with an overall height h8 of about 3.55 inches to about 4.34 inches, e.g., 3.94 inches, a width w3 of about 1.01 inches to about 1.23 inches, e.g., 1.12 inches, and a length l4 of about 1.03 inches to about 1.25 inches, e.g., 1.14 inches. The walls of the main body 450 have a thickness t3 of about 0.054 inches to about 0.067 inches, e.g., 0.061 inches.

The elongate vertical portion 434 has a height h9 of about 2.64 inches to about 3.23 inches, e.g., 2.93 inches. The elongate vertical portion 434 includes a lower section 490 and an upper section 492. The lower section 490 extends from a first end 493, which terminates at an interface with the bottom region 450, to a second end 494, which terminates at an interface with the upper section 492. The lower section 490 has a height h10 of about 2.37 inches to about 2.90 inches, e.g., 2.63 inches. At its first end 493, the lower section 490 has an inner diameter d4 of about 0.59 inches to about 0.72 inches, e.g., 0.65 inches. At its second end 494, the lower section 490 has an inner diameter d5 of about 0.56 inches to about 0.69 inches, e.g., 0.63 inches. That is, the walls of the lower section 490 taper inwardly at an angle 4 of about 0.45° to about 0.55°, e.g., 0.50°, along the centerline of the elongate vertical portion 430.

The upper section 492 has a height h11 of about 0.27 inches to about 0.33 inches, e.g., 0.30 inches. The upper section 492 tapers inwardly along the centerline of the elongate vertical portion 434, from the second end 494 of the lower section 490 to a top end 495 of the main body 446, at an angle $\theta_5$ of about 0.45° to about 0.55°, e.g., 0.50°.

The bottom region 450, including the base portion 452 and the flared portion 438, has an overall height h12 of about 0.91 inches to about 1.11 inches, e.g., 1.01 inches, with the base portion 452 having a height h13 of about 0.34 inches to about 0.41 inches, e.g., 0.38 inches, and the flared portion 438 having a height h14 of about 0.57 inches to about 0.70 inches, e.g., 0.63 inches.

The flared portion 438 extends from the first end 493 of the lower section 490 to an upper end 496 of the base portion 452. A first side of the flared portion 438 extends outwardly from the elongate vertical portion 434 at an angle $\theta_6$ of about 27° to about 33°, e.g., 30°, relative to the centerline of the elongate vertical portion 434, such that the flared portion 438 has an inner diameter d4 about 0.59 inches to about 0.72 inches, e.g., 0.65 inches at an upper end 458 of the bottom region 450 and has an inner diameter d6 of about 0.91 inches to about 1.11 inches, e.g., 1.01 inches at the junction with the base portion 452. The base portion 452 has inner diameter d6.

Figure 11A:
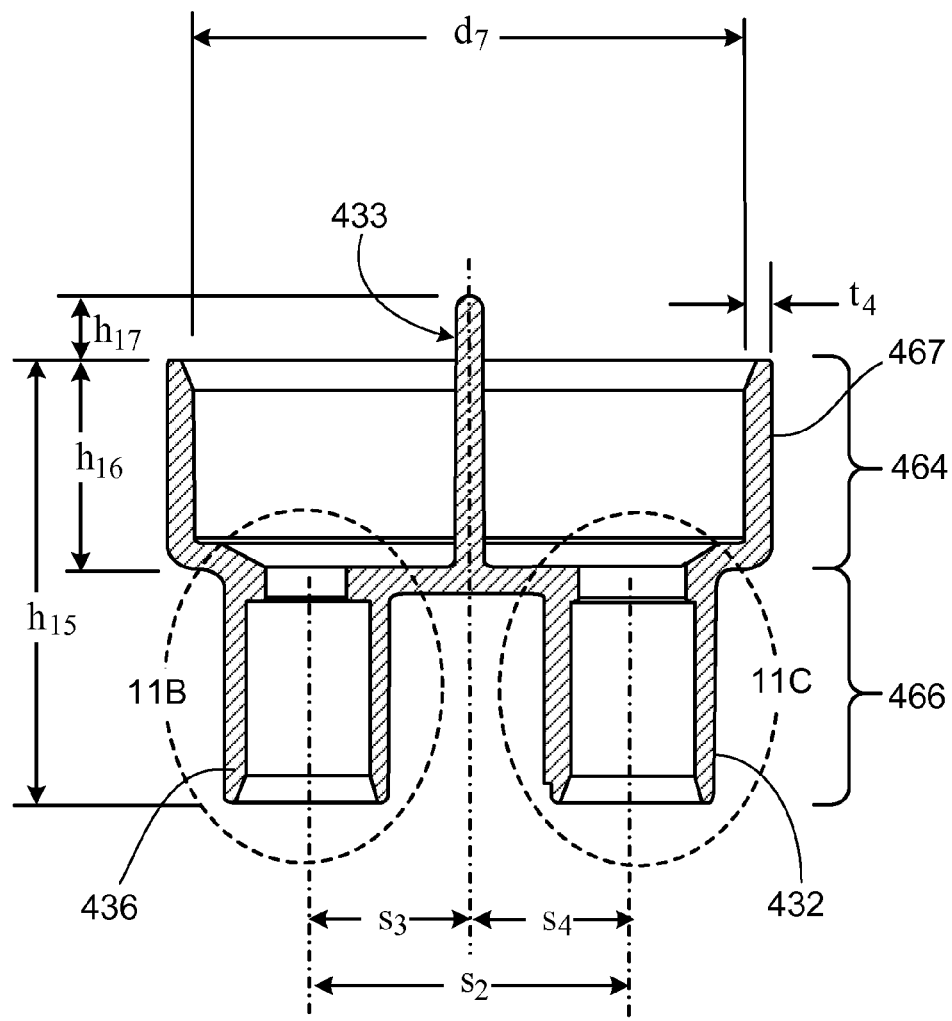
FIG. 11A is a cross-sectional side view of the two-port cap of FIG. 9.
Figure 11B:
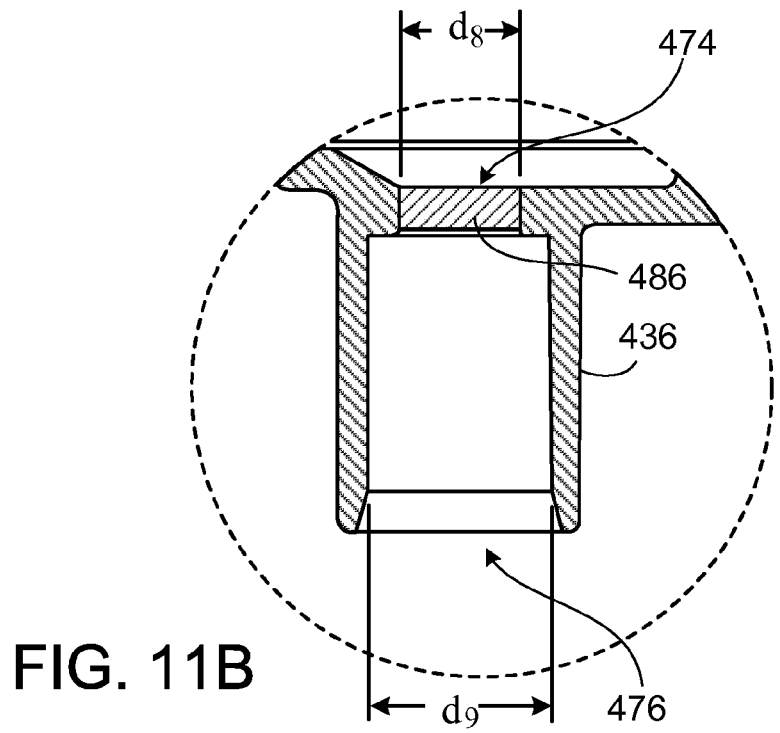
FIG. 11B is a detailed cross-sectional side view of an outlet port of the two-port cap of FIG. 11A.
Figure 11C:
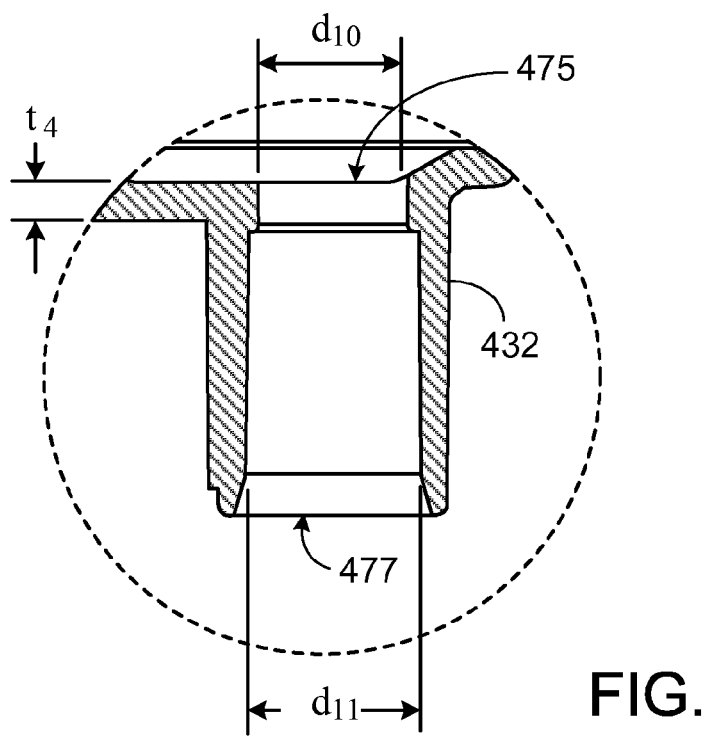
FIG. 11C is a detailed cross-sectional side view of an inlet port of the two-port cap of FIG. 11A.

Referring to FIGS. 11A-11C, the two port cap 444 has an overall height h15 of about 0.931 inches to about 1.137 inches, e.g., 1.034 inches, and an overall diameter d7 of about 1.12 inches to about 1.36 inches, e.g., about 1.24 inches, and includes an upper region 464 and a lower region 466. The upper region 464 includes an interface section 467, which interfaces with the base portion 452 of the main body 446, having a height h16 of about 0.433 inches to about 0.529 inches, e.g., 0.481 inches. The two port cap 444 also includes the inlet port 432 and the outlet port 436. The walls of the two port cap 444 have thickness t4 of about 0.054 inches to about 0.067 inches, e.g., 0.061 inches.

The centerline of the outlet port 436 is arranged at a distance s3 of about 0.30 inches to about 0.37 inches, e.g., about 0.33 inches from a centerline of the two port cap 444. The outlet port 236 includes a first counter bore hole 474 having a diameter d8 of about 0.210 inches to about 0.215 inches, e.g., 0.212 inches, Which extends from an interior of the two port cap 444, and a second counter bore hole 476 having diameter d9 of about 0.230 inches to about 0.282 inches, e.g., 0.256 inches, which extends from an exterior of the two port cap 444.

The centerline of the inlet port 432 is arranged at a distance s4 of about 0.60 inches to about 0.73 inches, e.g., 0.66 inches, from the centerline of the outlet port 436. The inlet port 432 includes a first counter bore hole 475 having a diameter d10 of about 0.150 inches to about 0.184 inches, e.g., 0.167 inches, which extends from an interior of the two port cap 444, and a second counter bore hole 477 having diameter d11 of about 0.230 inches to about 0.282 inches, e.g., 0.256 inches, which extends from an exterior of the two port cap 444.

A dam 433 is centered between the inlet port 432 and the outlet port 436 and extends at a height h17 of about inches to about inches, e.g., 0.125 inches, above the interface section 467. The dam 433 is sized to contact opposing side walls of the base portion 452 of the main body 446, such that all fluid entering through the inlet port 432 is flows over the top of the dam 433 before flowing out of the outlet port 436, which may help to contribute to the recirculation of un-released air bubbles.

Referring again to FIG. 8, when the two port cap 444 and the main body 446 are brought together they form the gas release device 430. A clot filter 486 (shown in FIG. 11B) is positioned within the first counter bore hole 474 of the outlet port 436. Fluid flows through the clot filter 486 prior to flowing out of the outlet port 436.

Figures 12A, 12B:
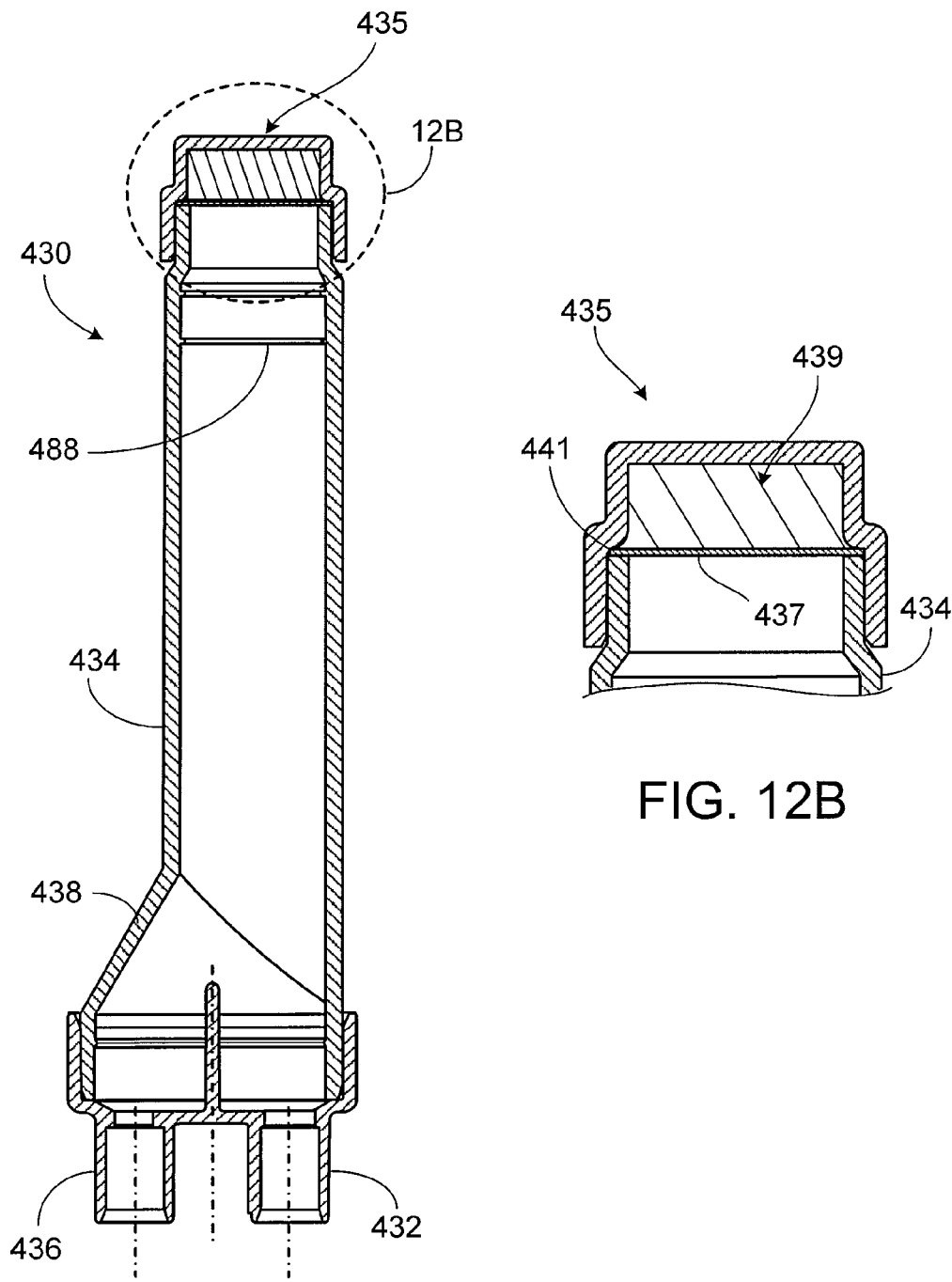
FIG. 12A is a side view of a gas release device and a vent assembly.
FIG. 12B is a detailed view of the vent assembly of FIG. 12A.

In some implementations, the gas release device may also include a vent assembly. For example, FIGS. 12A & 12B illustrate an implementation in which a vent assembly 435 is mounted to the top of the gas release device 430. Referring to FIG. 12B, the vent assembly 435 includes a micro-porous membrane 437, a vent structure 439, and a cap 441, which receives and supports the micro-porous membrane 437 and the vent structure 439. The cap 441 is configured to interface with the top (e.g., the upper section 492, of the elongate vertical portion 434.

The vent structure 439 is a solid porous block, having an average pore size of about 15 micron to about 45 microns, that allows air to pass through and escape from the gas release device. The vent structure 439 is also a self-sealing vent structure. In some implementations, the vent structure 439 is formed of a blend of polyethylene (e.g., high density polyethylene (HDPE)) and carboxymethylcellulose (CMC), a blend of polystyrene and methyl-ethyl-cellulose or of polypropylene- or polyethylene-based porous material. Such materials are available from Porex Corporation, Fairburn, Ga., such as EXP-816, which is a product containing 90% by weight polyethylene and 10% by weight carboxymethylcellulose with an average pore size of about 30 microns to about 40 microns. However, other percentages of the materials can be used, as well as other materials and other pore sizes. For example, the vent structure 439 can include about 80% to about 95% by weight high density polyethylene and about 5% to about 20% by weight carboxymethylcellulose.

When the vent structure 439 comes into contact with liquid, e.g., humidity or moisture, the swelling agent (e.g., cellulose component, e.g., carboxymethylcellulose) of the vent structure expands, thereby closing off the pores in the polymer component (e.g., high density polyethylene) of the vent structure 439. The vent structure 439 is mounted adjacent to and just above the hydrophobic membrane 437 so that the hydrophobic membrane 437 is located between the vent structure 439 and the gas release device 430. The vent structure 439 inhibits (e.g., prevents) condensation from accumulating on and contacting the membrane 437. In some implementations, the vent structure 439 directly contacts the membrane 437. The vent structure 439 can be substantially disc shaped or can be another shape that is compatible with a device on which the vent structure 439 is mounted. In some implementations, the vent structure 439 is about 0.1 mm to about 10 mm thick.

When the gas release device 430 is filled with blood, inhibiting (e.g., preventing) the protein in the blood from accumulating on the membrane 437 can maintain the hydrophobic characteristic of the membrane 437. Whole blood can be kept from the membrane 437 by providing a barrier between the blood and the membrane 437, such as a liquid barrier 488. The height of the gas release device 430 is sufficient to maintain this barrier 488 and inhibits (e.g., prevents) the liquid above the barrier 488 from substantially mixing with liquid below the barrier 488.

In some implementations, the gas release device and one or more other components can be incorporated into an integrated fluid circuit. The integrated fluid circuit has the components described above, such as the gas release device, formed together in one assembly or integrated molding rather than discrete separate or modular devices. The integrated fluid circuit is adapted to removably seat into a machine, such as a blood purification machine, like a hemodialysis machine. The integrated fluid circuit is similar to a cassette or cartridge, where an operator merely snaps the integrated fluid circuit into the machine and after just a few additional connections, begins operation.

Figure 13C:
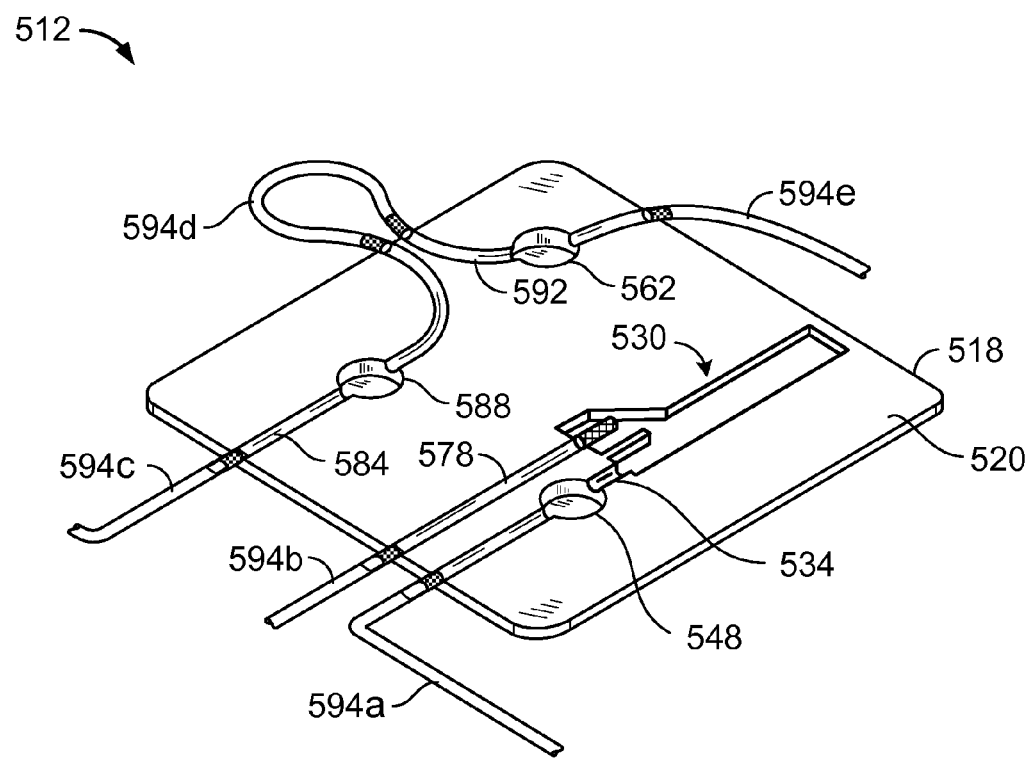
FIG. 13C is a perspective view of the cassette-like integrated extracorporeal circuit of FIG. 13A.

Referring to FIGS. 13A-13C, the integrated fluid circuit 512 has a rigid body 518 and a flexible backing (not shown). The rigid body has a substantially flat surface 520 with one or more concave (when viewed from the backside) portions or recessed portions protruding from a front surface of the body 518. The flexible backing can be applied so that the backing covers only the recessed portions or so that the backing covers more than just the recessed portions, up to all of the back surface of the rigid body.

The integrated fluid circuit has a recessed portion that serves as the gas release device 530. Due to its relatively flat design, the gas release device described above with regard to FIGS. 2A-7B lends itself to be molded into a cassette-like configuration. The gas release device 530 of FIGS. 13A-13C can have the same general dimensions as the gas release device described above with regard to FIGS. 2A-7B.

A first channel 534 in rigid body 518 leads from an edge of the rigid body 518 to a bottom region of the gas release device 530. Over one portion of the channel 534, a venous recess or pocket 548 is formed. The flexible backing backs the venous pocket 548. The venous pocket 548 is sized so that a transducer in the machine can measure the venous fluid pressure through the flexible backing. A second channel 578 extends from the outlet of the gas release device 530 to an edge of the rigid body 518. The first and second channels extend to the same or different edges of the rigid body 518. The first channel 534 and second channel 578 are in fluid communication with the gas release device 530.

In some implementations, a third channel 584 is formed in the rigid body 518. The third channel 584 is not in fluid communication with the first or second channels when the integrated fluid circuit is not in the machine or connected to a dialyzer. In some implementations, an arterial pocket 588 is formed along the third channel 584. The arterial fluid pressure can be measured through the flexible backing of the arterial pocket 588. One end of the third channel 584 extends to one edge of the rigid body 518 and the other end extends to the same or a different edge, as shown in FIGS. 13A-13C.

Optionally, a fourth channel 592 extends across the rigid body 518. A post-pump arterial pocket 562 overlaps the fourth channel 592. In some implementations, additional recesses and channels are formed in the rigid body.

In some implementations, tubes 594a, 594b, 594c, 594d and 594e are connected to the rigid body 518, such as at the locations where the first, second, third and fourth channels extend to the edges. The tubes are connected to the rigid body using techniques known in the art. In some implementations, the tubes fit into a pre-formed grooves in the rigid body 518. The tubes can be pressure fitted into the grooves. In other implementations, the tubes are clipped onto the rigid body 518. Optionally, at the end of the tubes 594a, 594b, 594c and 594e are fasteners for connecting the tubes to components of the machine, such as the dialyzer or to a patient. Tube 594d wraps around a peristaltic pump in the machine. Tubes 594a and 594e connect to a dialyzer. Tubes 594b and 594c connect to a patient.

Certain extracorporeal circuits described above include a drip chamber positioned along the arterial portion of the extracorporeal circuit in addition to the gas release device positioned on the venous side of the extracorporeal circuit. However, it should be understood that, in certain implementations, no such drip chamber is provided on the arterial side of the extracorporeal circuit. The gas release device on the venous side of the extracorporeal circuit can, for example, be the only venting device provided along the extracorporeal circuit.

The components described herein can be used with other liquids, such as plasma, water, saline, and other medical fluids. Additionally, liquids other than saline can be used to prime the system.

Other implementations are within the scope of the following claims.

What is claimed is:
1. A gas release device for removing gas from a bodily liquid in extracorporeal circuitry, the gas release device comprising:
an elongate vertical portion;
a flared portion extending outwardly from the elongate vertical portion;
an inlet port for delivering a bodily liquid into the gas release device; and
an outlet port for evacuating the bodily liquid from the gas release device,
wherein the inlet port is positioned below the elongate vertical portion and the outlet port is positioned below the flared portion such that bodily liquid traveling from the inlet port toward the outlet port is forced around the flared portion to cause gas bubbles in the bodily liquid to be re-circulated back toward the inlet port, and the elongate vertical portion has a height sufficient to maintain an interface between a first liquid in the gas release device and a second liquid in the gas release device when the first and second liquids are miscible and the second liquid is flowing through the gas release device.

2. The gas release device of claim 1, wherein the gas release device has a substantially flat geometry.

3. The gas release device of claim 1, wherein the gas release device has a substantially tubular geometry.

4. The gas release device of claim 1, wherein the elongate vertical portion has a height of about 2.54 inches to about 3.10 inches.

5. The gas release device of claim 4, wherein the elongate vertical portion has a height of 2.82 inches.

6. The gas release device of claim 1, wherein the elongate vertical portion has a hollow volume of about 0.70 cubic inches to about 1.33 cubic inches.

7. The gas release device of claim 1, wherein a first side of the flared portion extends outwardly from the elongate vertical portion at an angle of about 44° to about 54° relative to a centerline of the elongate vertical portion.

8. The gas release device of claim 7, wherein the first side of the flared portion extends outwardly from the elongate vertical portion at an angle of 49° relative to the centerline of the elongate vertical portion.

9. The gas release device of claim 1, wherein a first side of the flared portion extends outwardly from the elongate vertical portion at an angle of about 27° to about 33° relative to a centerline of the elongate vertical portion.

10. The gas release device of claim 9, wherein the first side of the flared portion extends outwardly from the elongate vertical portion at an angle of 30° relative to the centerline of the elongate vertical portion.

11. The gas release device of claim 1, wherein the gas release device comprises:
a main body, which defines the elongate vertical portion and the flared portion; and
a two port cap, which defines the inlet and outlet ports.

12. The gas release device of claim 1, wherein the inlet port is elevated above the outlet port with respect to the standard orientation of the gas release device.

13. The gas release device of claim 12, wherein the inlet port is elevated at a height of about 0.29 inches to about 0.35 inches above the outlet port.

14. The gas release device of claim 1, wherein a bottom wall of the gas release device extends at an angle of about 54° to about 66° relative to vertical, with respect to the standard orientation of the gas release device.

15. The gas release device of claim 14, wherein the bottom wall of the gas release device extends at an angle of 60° relative to vertical, with respect to the standard orientation of the gas release device.

16. The gas release device of claim 1, further comprising a dam between the inlet port and the outlet port.

17. The gas release device of claim 1, further comprising a clot filter positioned in the gas release device, the clot filter positioned so that the liquid passes through the clot filter prior to passing through the outlet port.

18. The gas release device of claim 1, wherein the gas release device is incorporated as a component in a cassette-like integrated fluid circuit adapted to removably seat in a bodily liquid purification machine.

19. A method of removing gas from blood in extracorporeal circuitry, comprising:
passing a blood-compatible component through an inlet port of a gas release device, thereby filling the gas release device so that substantially no gas remains in the gas release device; then
passing blood through the inlet port and into an elongate vertical portion of the gas release device until upward motion of the blood is impeded by gravity, thereby forming a liquid-liquid interface between the blood-compatible component and the blood; and
passing the blood along a flared portion of the gas release device toward an outlet port such that gas bubbles in the blood are directed back toward the inlet port to be released through the elongate vertical portion.

20. The method of claim 19, wherein passing the blood-compatible component through the inlet port includes passing saline through the inlet port.

21. The method of claim 19, further comprising:
forcing the blood over a dam after passing the blood through the inlet port; and
passing the blood out the outlet port after forcing the blood over the dam.

22. The method of claim 19, further comprising:
passing the blood through a clot filter; and
passing the blood through the outlet port after passing the blood through the clot filter.

23. The method of claim 19, wherein the inlet port of the gas release device is elevated relative to the outlet port of the gas release device.

24. A gas release device for removing gas from a bodily liquid in extracorporeal circuitry, the gas release device comprising:
a main body that defines an elongate vertical portion and a flared portion extending outwardly from the elongate vertical portion; and
a two port cap that defines an inlet port for delivering a bodily liquid into the gas release device and an outlet port for evacuating the bodily liquid from the gas release device,
wherein the inlet port is positioned below the elongate vertical portion and the outlet port is positioned below the flared portion such that bodily liquid traveling from the inlet port toward the outlet port is forced around the flared portion to cause gas bubbles in the bodily liquid to be re-circulated back toward the inlet port.

25. The gas release device of claim 24, wherein a first side of the flared portion extends outwardly from the elongate vertical portion at an angle of about 44° to about 54° relative to a centerline of the elongate vertical portion.

26. The gas release device of claim 24, wherein a first side of the flared portion extends outwardly from the elongate vertical portion at an angle of about 27° to about 33° relative to a centerline of the elongate vertical portion.

* * * * *